United States Patent [19]

Miyakawa et al.

[11] Patent Number: 4,640,129
[45] Date of Patent: Feb. 3, 1987

[54] METHOD AND APPARATUS FOR DETECTING TONER CONCENTRATION OF TWO-COMPONENT DRY DEVELOPER

[76] Inventors: Seiichi Miyakawa, 1346 Kagawa, Nagareyama-shi, Chiba; Susumu Tatsumi, 17-9 Hinodai 5-chome, Hino-shi, Tokyo; Koji Sakamoto, 9-14 Chuoh 1-chome, Ohta-ku, Tokyo, all of Japan

[21] Appl. No.: 726,166

[22] Filed: Apr. 22, 1985

Related U.S. Application Data

[63] Continuation of Ser. No. 362,497, Mar. 26, 1982, abandoned, which is a continuation of Ser. No. 156,411, Jun. 4, 1980, abandoned, which is a continuation-in-part of Ser. No. 881,853, Feb. 27, 1978, abandoned.

[51] Int. Cl.$^4$ .......................... G01N 11/06; G03G 9/10
[52] U.S. Cl. ................. 73/866; 222/DIG. 1; 118/689; 324/202; 250/573; 73/861.04
[58] Field of Search ............... 222/52, 57, DIG. 1; 118/689, 690, 691; 355/3 DD, 14 D; 73/223, 861, 432 R, 432 Z, 861.04; 324/202; 250/573

[56] References Cited

U.S. PATENT DOCUMENTS

| | | | |
|---|---|---|---|
| 3,320,804 | 5/1967 | Halberstam | 250/573 X |
| 3,572,551 | 3/1971 | Gillespie et al. | 222/56 |
| 3,611,803 | 10/1971 | Kajiura et al. | 73/861.73 |
| 3,698,926 | 10/1972 | Furuichi | 118/689 X |
| 3,831,446 | 8/1974 | Dye | 73/861 |
| 3,999,687 | 12/1976 | Baer et al. | 222/DIG. 1 X |

OTHER PUBLICATIONS

Khoury et al, "Toner Concentration Sensor", IBM Tech. Disclosure Bulletin, vol. 13, No. 12, May 1971, p. 3607.

Primary Examiner—Joseph J. Rolla
Assistant Examiner—Frederick R. Handren
Attorney, Agent, or Firm—Wyatt, Gerber, Shoup, Scobey and Badie

[57] ABSTRACT

A method of detecting the toner concentration of a two-component developer comprising a mixture of carrier particles and toner particles for use in an electrostatic copying apparatus or the like wherein a relationship between flow rate and the toner concentration of a two-component developer which passes through a container is obtained in advance, then the flow rate of the two-component developer whose toner concentration is unknown is measured by use of the container and developer flow rate detecting member. Thus, the toner concentration of the developer is determined from the measured flow rate and the relationship between the flow rate and the toner concentration which has been obtained in advance.

12 Claims, 7 Drawing Figures

METHOD AND APPARATUS FOR DETECTING TONER CONCENTRATION OF TWO-COMPONENT DRY DEVELOPER

RELATED APPLICATIONS

This application is a continuation of copending application Ser. No. 06/362,497, filed Mar. 26, 1982 and now abandoned; which was a continuation of copending application Ser. No. 06/156,411, filed June 4, 1980 and now abandoned; which was a continuation-in-part of copending application Ser. No. 05/881,853, filed Feb. 27, 1978 and now abandoned.

BACKGROUND OF THE INVENTION

The present invention relates to improved methods of detecting the active toner concentration of a two-component developer comprising a mixture of carrier particles and toner particles including active and fatigued toner particles for use with an electrostatic copying apparatus or the like.

Conventionally, various attempts have been made to detect the active toner concentration of two-component developers. These include an optical method wherein a developer comprising carrier particles having a different color from that of toner particles is illuminated, and the mixing ratio of toner particles and carrier particles is detected by a reflected light from the developer; and a magnetic method wherein the mixing ratio of toner particles and carrier particles is detected through a change of the magnetic permeability of the developer.

Additionally, methods of measuring the density or specific gravity, or the conductance of the developer have been proposed.

However, in the optical method, the color of carrier particles has to be different from that of toner particles. Therefore, the kinds of carrier particles that can be employed in this method are limited, for example, to resin-coated carrier particles, and the development method therefor is also limited to some extent.

Moreover, the developer does not change much in color with a change of the toner concentration of the developer so that the detecting accuracy of the toner concentration is apt to be decreased.

The magnetic method is one of the most reliable methods that have been put to practical use. However, its detecting accuracy and sensitivity are not completely satisfactory.

In a method disclosed in Japanese Patent Sho-46-8280 and Japanese Laid-Open Patent Application Sho-51-19540, a developer that has been used in the development process is caused to pass through a non-magnetic cylinder around which a coil is wound and the mixing ratio of toner particles and carrier particles of the developer is detected by a change of the inductance of the coil. A somewhat similar procedure is described in U.S. Pat. No. 3,999,687.

This method utilizes the phenomenon that the magnetic permeability of the developer that passes through the non-magnetic cylinder changes in accordance with the content of carrier particles in the developer. In other words, the phenomenon that a change of the toner concentration gives rise to a change of the bulk density of the developer is utilized.

However, in the case of the developers which are usually used, the toner concentration is in the range of from 1 to 3 wt %, and the change of the bulk density is as low as approximately 7 to 8% for each 1 wt % change of toner concentration, since the specific gravity of the carrier particles is about 7 to 8 times that of the toner particles.

The difficulty with procedures such as these, which depend upon measurement of change in inductance is that such measurements are not capable of distinguishing between fatigued and active toners. The reason for this is that inductance depends upon the presence of magnetic carrier particles, not upon the presence of toner, and as pointed out above, there is very little change in the content of the carrier particles in the developer with change in toner concentration. Moreover, procedures which depend solely upon inductance measurements to determine toner concentration are not capable of distinguishing between fatigued and active toner particles since the inductance value determined is dependent upon the change in carrier concentration, and the toner concentration is determined as the difference between the initial toner and carrier concentration and the change in carrier concentration as measured by change in inductance.

SUMMARY OF THE INVENTION

It is therefore a principal object of the present invention to improve the methods and apparatus for detecting the toner concentration of two-component developers.

Another object of the present invention is to provide toner concentration detectors which detect the flow rate of developer.

According to the method of the present invention, unlike the conventional method, the flow rate of the developer is measured. It has been observed that flow rate changes greatly in accordance with the change of active toner concentration. The flow rate is measured by the period of time required for a predetermined amount of the developer to be discharged from a container, or by the amount of the developer discharged from the container in a unit time.

More specifically, in one method according to the present invention, a predetermined amount of the developer is placed in a container and is then discharged from an outlet of the container through an active toner concentration detector disposed under the outlet of the container. In one embodiment, the active toner concentration detector comprises an elastic plate with a strain gauge pasted thereon, which can be bent by the force applied thereto by the flow of the developer from the container, producing an electric current for measurement of the above-mentioned flow rate.

Another embodiment of an active toner concentration detector according to the invention comprises a non-magnetic cylinder connected to the container, through which the developer flows, and around which is wound a coil for detecting changes of the magnetic permeability inside the non-magnetic cylinder which are caused by the flow of the developer with a different active toner concentration. This toner concentration detector also detects the above-mentioned flow rate of the developer through the changes of the magnetic permeability.

A further embodiment of a toner concentration detector comprises a non-magnetic cylinder with an oscillator circuit, a frequency detector, a reference circuit, a comparison circuit and a driving circuit. The oscillator circuit is composed of a coil wound around the non-magnetic cylinder and a capacitor. It is connected to the frequency detector. The frequency detector detects a frequency produced by the oscillator circuit in accordance with the toner concentration. The reference circuit produces a predetermined frequency corresponding to an active desired toner concentration, and the comparison circuit compares an output from the frequency detector and that from the reference circuit to give a signal to the driving circuit so that the replenishment of toner particles to be made to the developer is controlled.

The above-mentioned active toner concentration detector can be replaced by a photoelectric detection apparatus composed of a light emission diode and a light receiving element.

According to the invention, the active toner concentration can be found from the flow rate of the developer. The sensitivity of the detection of the active toner concentration is high and accordingly its accuracy is also high.

In accordance with the invention, the flow rate of the developer which varies in accordance with the differences in particle size between active toner particles, fatigued toner particles and carrier particles is measured. In the case of a two-component developer in which the toner component is a magnetic toner, the flow rate can also be accurately measured. Any development method conventionally employed with two component developers can be used.

In the conventional method in which the toner concentration is determined by the bulk density of the developer, it has been observed that as the number of copies increases to 5,000 or 10,000, the toner concentration which has been initially set at 1 wt % increases to more than 2 wt %. If an attempt is made to maintain the toner concentration at 1 wt %, the bulk density of the developer changes greatly from 3.6 g/cm$^3$ to 4 g/cm$^3$. This contributes to the inaccuracies of the method.

Other objects and further scope of applicability of the present invention will become apparent from the detailed description given hereinafter. It should be understood however, that the detailed description and specific examples, while indicating preferred embodiments of the invention, are given by way of illustration only, since various changes and modifications within the spirit and scope of the invention will become apparent to those skilled in the art from this detailed description.

This invention will be best understood from a consideration of the use of inductance measurements to determine flow rate and changes in flow rate in accordance with the concept of the invention.

Initially, however, it is necessary to understand the contents of a developer and how they change during use. A developer as prepared, comprises a relatively small amount of relatively small active or effective toner particles together with a relatively large amount of carrier particles. The latter are normally magnetic so that when they flow through a coil, a current will be produced and the inductance of the coil can be measured. The developer will have an initial flow rate which depends upon the amount and relative size of the toner and carrier particles.

As the developer is used, the toner is employed to form images. Certain amounts of the toner, however become "fatigued" and are not useful for the production of images. Fatigued particles form larger particles by agglomeration of smaller toner particles. There are therefore, two principal physical changes in the characteristics of the developer. One is that the relative amount of carrier particles increases, the other is that the relative amount of large particles increases.

Considered in terms of inductance, the effect of the first change is to increase the inductance. It would appear therefore, that increase in inductance should be a measure of toner concentration. In fact it is. The difficulty however, is that this measurement does not distinguish between active toner and fatigued toner.

The second change affects flow rate of the developer since the smaller the number of small particles, i.e. the less amount of active toner particles, the larger will be the number of large particles, i.e. fatigued toner particles and carrier particles, and the greater will be the rate at which a unit volume of the developer will flow past a particular point.

It follows from the foregoing that changes in flow rate can be used to accurately measure changes in active toner concentration. Changes in inductance, however, cannot be employed so accurately. It does not follow, however, that changes in inductance cannot be used to measure changes in flow rate. The point is, that it is not possible to go directly from a change in inductance to a change in active toner concentration without knowledge of how changes in active toner concentration affect changes in flow rate. If a standard curve is prepared showing changes in flow rate with changes in active toner concentration, one may thereafter use changes in inductance, a strain gauge, an oscillator circuit or other means to determine the concentration of active toner in a developer.

The flow rate of the developer can be defined either by the amount which flows during a specific time, e.g. cm$^3$/sec, or by the time required for a specific amount to flow, e.g. sec/cm$^3$. If the former definition is indicated by F, the latter is the reciprocal of F, or 1/F. From the above, it follows that as the active toner concentration increases, F decreases and 1/F increases. This change of flow rate indicates the change in the concentration of small particles, i.e. effective toner in the developer.

It should be noted in connection with the above, that merely measuring a change in flow rate does not permit an accurate determination of change in active toner concentration. It is necessary to first establish a standard curve. The standard curve will, of course, vary with different developers.

DETAILED DESCRIPTION OF THE PREFERRED EMBODIMENTS

Figure 1:
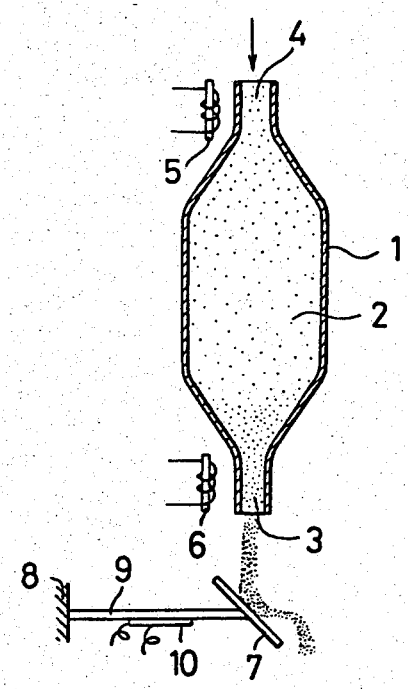
FIG. 1 is a schematic sectional side elevation of an embodiment of a toner concentration detector according to the present invention.

Referring to FIG. 1, reference numeral 1 represents a container with a predetermined capacity for holding a two-component developer 2 containing magnetic carrier particles. At the lower portion of the container 1 is formed an orifice 3 with a narrow outlet, and at the upper portion of the container 1 is formed an inlet portion 4. Electromagnets 5, 6 are disposed at the respective sides of the orifice 3 and the inlet portion 4. Under the orifice 3 is disposed an inclined receiving plate 7 which is mounted at the tip of an elastic plate 9 fixed to a base portion 8. A strain gauge 10 is applied to the plate 9.

When the concentration of active toner is to be detected, the electromagnet 6 is energized so that the developer 2 is not permitted to pass through the orifice 3. The electromagnet 5 is then deenergized and the developer 2 is permitted to flow in the container through the inlet portion 4. Thus, the container 1 is filled with a predetermined amount of the developer 2. The electromagnet 5 is then energized, but the magnet 6 is deenergized, whereby the developer 2 is caused to flow from the container 1 through the orifice 3. A force is applied to the receiving plate 7 by the developer 2 which flows out of the container 2, with the result that the support 9 is bent, and the strain gauge 10 detects that the developer 2 is flowing down. The period of time from the start of the flow of the developer to the end thereof is detected by an electric circuit (not shown).

Figure 2:
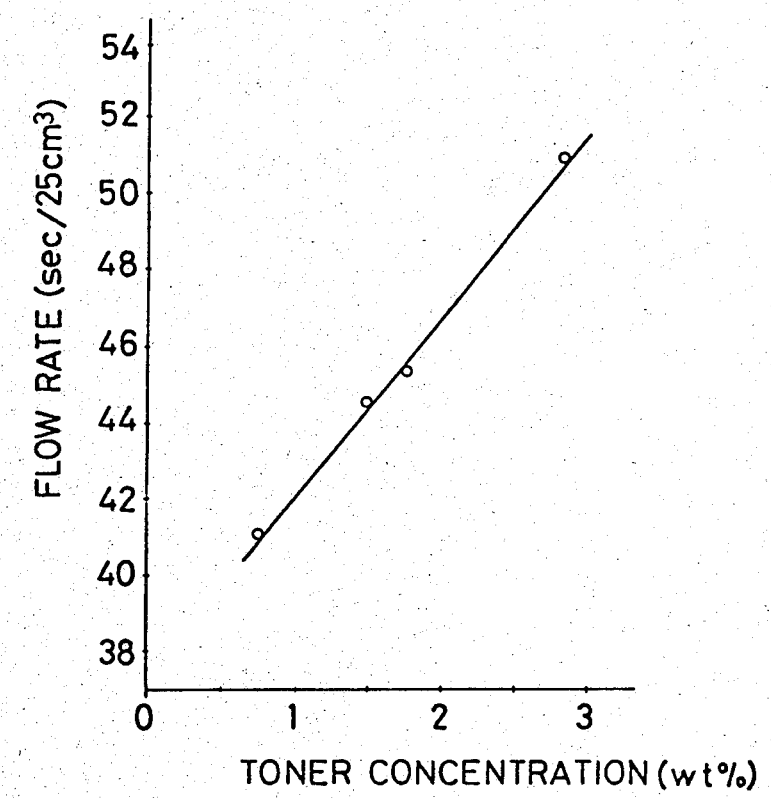
FIG. 2 shows the data of a relationship between the toner concentration and the flow rate of a two-component developer.

Referring now to FIG. 2, the data of the relationship between active toner concentration and flow rate of the developer 2 are plotted, with active toner concentration as abscissa and flow rate as ordinate, when 25 cm$^3$ of the developer was caused to flow from the container 1. Here the toner concentration is defined as percent by weight of active toner contained in the developer 2 and the flow rate as a period of time (sec) taken for 25 cm$^3$ of the developer 2 to be completely discharged from the container 1. Thus, the unit of the active toner concentration is wt % and that of the flow rate is sec/25 cm$^3$ in FIG. 2.

As can be seen from the graph of FIG. 2, the flow rate increases with the increase of the active toner concentration. In other words, the higher the active toner concentration, the longer the time required for the developer 2 to be discharged from the container 1. Therefore, by measuring the flow rate, the active toner concentration can be detected.

Figure 3:
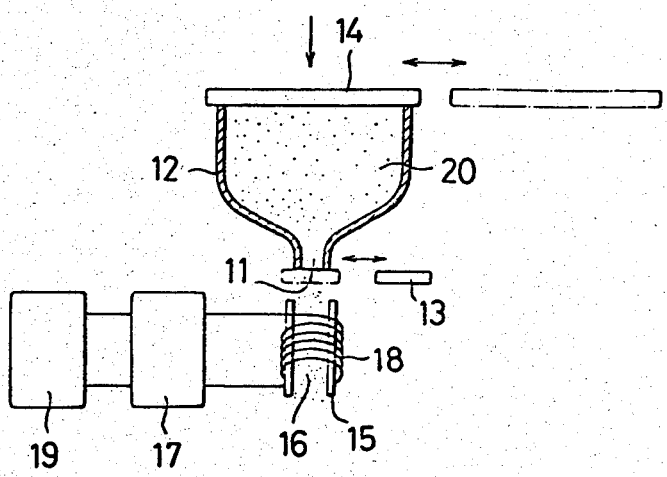
FIG. 3 is a schematic sectional side elevation of another embodiment of a toner concentration detector of the invention.

Referring now to FIG. 3, there is shown another embodiment of an active toner concentration detector of the present invention. In the figure, a container 12 with a predetermined capacity is provided, in which an orifice 11 with a predetermined size aperture is formed at the lower portion of the container 12. Lids 13, 14 which can be slidably opened, are disposed on the lower end and the upper ends of the container 12, respectively. Under the orifice 11 is arranged a cylinder 15 made of a non-magnetic material which forms a developer flow passage 16. Around the cylinder 15 is arranged a coil 18 which is connected to a frequency detector 17. The frequency detector 17 is connected to a flow rate measurement apparatus 19.

Detection of the active toner concentration by use of this detector can be carried out as follows. The lower end of the container 12 is closed by the lid 13 and developer 20 is placed in the container 12. The lid 14 is then closed so that a predetermined amount of the developer 20 is held in the container 12. By opening the lid 13, the developer 20 is caused to flow from the container 12 through the orifice 11. The magnetic permeability inside the cylinder 15 varies depending upon whether only air is present or the developer 20 is also present inside the cylinder 15. A frequency generated by an oscillation circuit disposed inside the frequency detector 17 is set so as to become a resonance frequency when the developer 20 passes through the cylinder 15. From the resonance frequency, the flow rate is measured and the active toner concentration of the developer can be determined since, as described above, there is a correlation between the active toner concentration and the flow rate of the developer.

In the above-mentioned respective embodiments, a more homogeneous discharge of the developer can be attained by applying constant vibrations to the respective containers 1 and 12.

Figure 4:
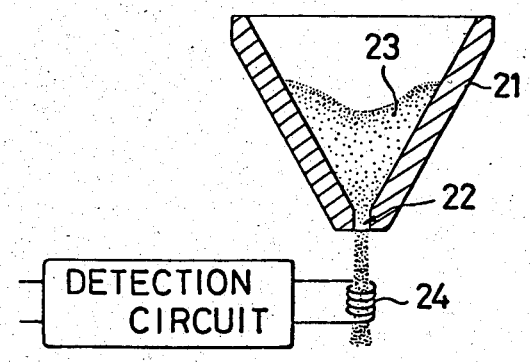
FIG. 4 is a schematic sectional side view of another embodiment of a toner concentration detector of the invention.

FIG. 4 illustrates schematically a further embodiment of the present invention, in which reference numeral 21 represents a funnel-shaped hopper with an approximate vertical angle of 60°.

At the lower portion of the hopper 21 is formed an outlet which measures 2.5 mm in diameter and 3 mm in length. Generally, such an apparatus is called Hall's flow meter. In the hopper 21 is held 50 grams of a two-component developer 23 comprising a mixture of ferromagnetic carrier particles with a particle size of approximately 100μ and toner particles with a particle size of approximately 10μ.

Under the outlet 22 of the hopper 21 is arranged a coil 24 which forms a circular passageway for the developer which flows from the outlet 22. By detecting the changes of the inductance of the coil 24, the period of time taken for all the developer 23 to be discharged from the hopper 21 is measured.

Figure 5:
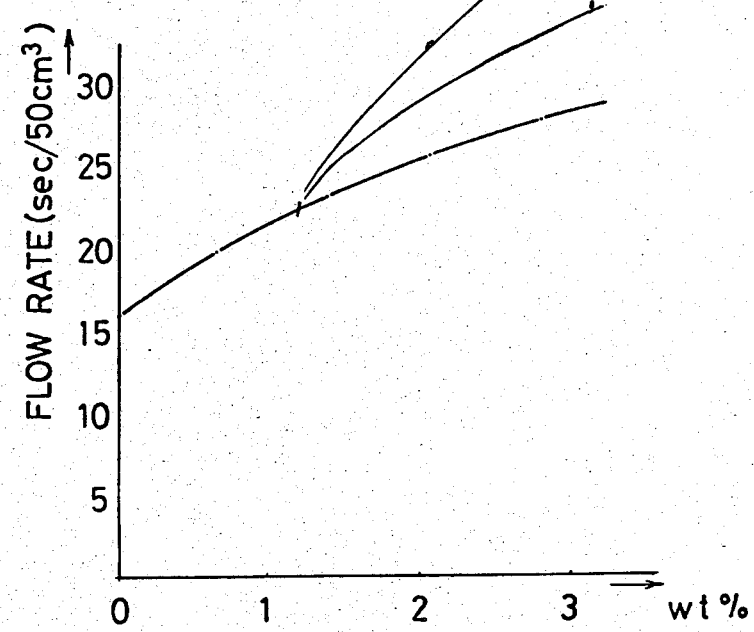
FIG. 5 shows another data of a relationship between the toner concentration and the flow rate of a two-component developer.

In one instance, the flow rate of the developer was measured by changing the toner concentration in the range of from 0 to 3 wt %. The results are shown in FIG. 5. In the figure, the flow rate of the developer is plotted as ordinate and the toner concentration as abscissa. As can be seen from the figure, in the range from 1 to 3 wt % of the toner concentration, the flow rate changes by approximately 20% by the change of 1 wt % of the toner concentration. This change corresponds to about 2 to 4 times that of the volume of the developer.

Thus, it is found that in accordance with the change of the active toner concentration, the quantity of the ferromagnetic carrier particles which flow out of the hopper 21 in a unit time also changes. It can be presumed that this is because of the viscosity of the developer when it flows out of the outlet 22. In other words, when the active toner concentration is low, the developer easily flows out through the outlet 22 and accordingly, the quantity of the ferromagnetic carrier passing through the outlet 22 in a unit time increases.

Figure 6:
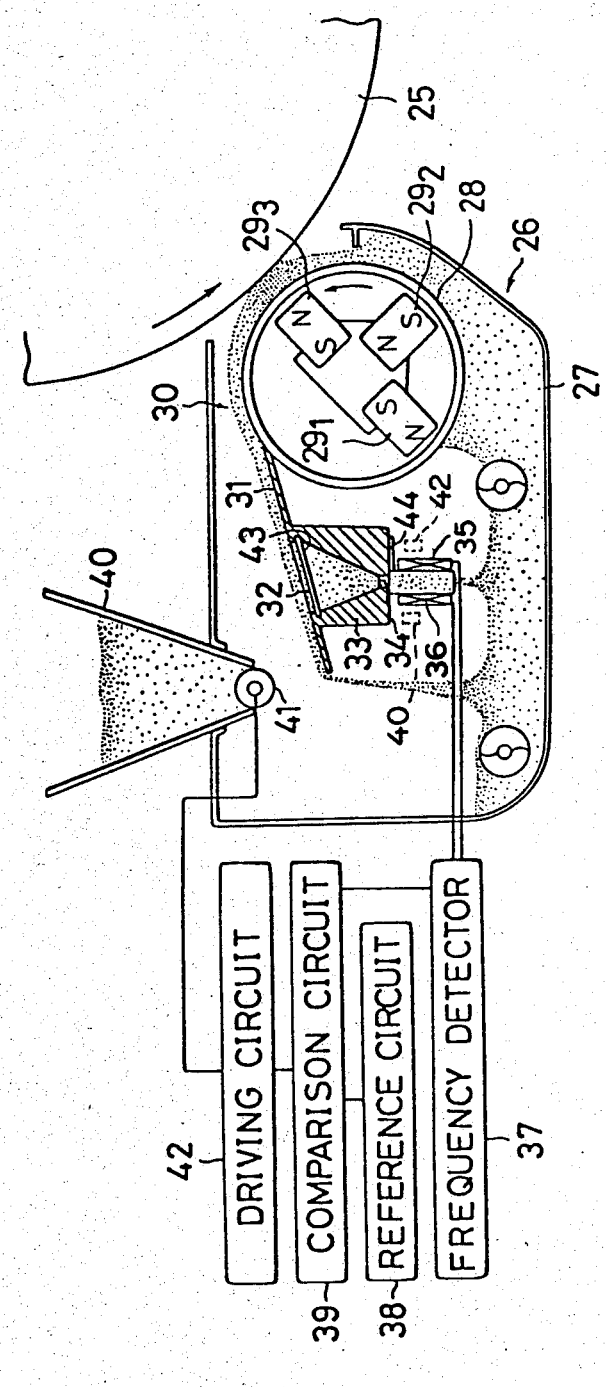
FIG. 6 is a schematic sectional side elevation including a block diagram of a further embodiment of a toner concentration detector of the invention, which is incorporated in a development apparatus.

In FIG. 6, reference numeral 25 represents a photoconductive drum which is rotated continuously in the direction of the arrow. On the surface of the drum is formed a latent electrostatic image by charging exposure, and other conventional means.

In the figure, a magnetic brush development apparatus 26 is disposed under the left side of the photoconductive drum 25.

The latent electrostatic image formed on the photoconductive drum 25 is developed by the magnetic brush development apparatus 26. The magnetic brush development apparatus 26 has a development roller 30 which comprises a non-magnetic cylindrical sleeve 28 disposed in a development tray 27 and a plurality of magnets $29_1$, $29_2$, $29_3$ disposed in the sleeve 28. By the magnets $29_1$, $29_2$, $29_3$, a magnetic brush is formed on the surface of the sleeve 28 which is rotated in the direction of the arrow. A scraper 31 is disposed in close vicinity to or in contact with the surface of the sleeve 28. In the approximate center of the scraper 31 is formed an opening 32 and under the scraper 31 is arranged a hopper 33 which is connected to the opening 32. The hopper 33 is funnel-like shaped similar to the hopper of FIG. 4. At the lower portion of the hopper 33 is formed an outlet 34 which measures 2.5 mm in diameter and 3 mm in length and under the outlet 34 is disposed a non-magnetic cylinder 35.

A coil 36 is wound around the cylinder 35, and is connected to a frequency detector 37 which detects a frequency generated by an LC oscillator circuit composed of a capacitor and the coil 36 having an inductance L. An output from the frequency detector 37 and that from a reference circuit 38 are compared by a comparison circuit 39, and in accordance with an output from the comparison circuit 39, a signal is given to a driving circuit 42 so as to control the rotation of a toner replenishing roller 41 disposed at the lower portion of a toner hopper 40.

Figure 7:
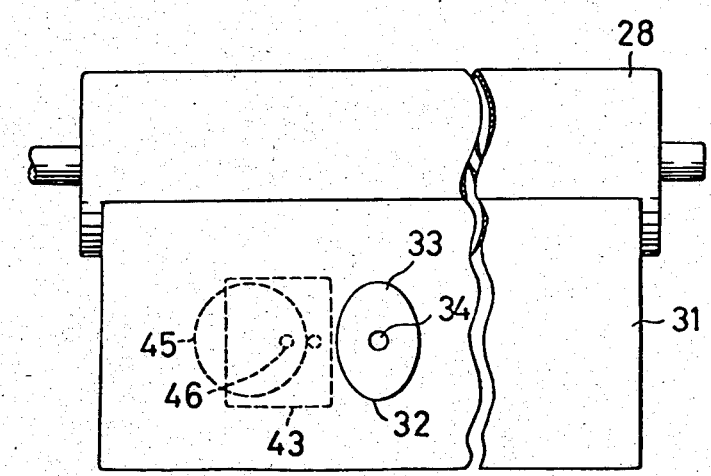
FIG. 7 is a schematic partial plan view of the development apparatus of FIG. 6.

A first movable shutter plate 43 is disposed above the hopper 31 as shown in FIGS. 6 and 7. Additionally, a second movable shutter plate 44 for closing the outlet 34 of the hopper 33 is disposed below the hopper.

The present apparatus is operated as discussed below. Normally, the first shutter plate 43 is located so as to prevent the developer conveyed by the scraper 31 from falling into the hopper 33 by covering the upper portion of the hopper 33 as illustrated in FIG. 6. At this moment, the second shutter plate 44 is retracted from the outlet 34. In this condition, the toner concentration is not detected. Thus, even if the first shutter plate 43 is opened, nothing happens so long as the detection circuits of toner concentration is not operated.

The first shutter plate 43 is closed in the following manner. As shown in FIG. 7, a cam 45 is rotated by 180° about a shaft 46, and the first shutter 43 is moved to the right by a pin of the first shutter plate 43 which is engaged with the cam 25 so that the opening 32 is closed.

Now entering into an active toner concentration detection step, the first shutter plate 43 is moved to a position indicated by dash lines in FIG. 7 and at the same time, the second shutter 44 is moved so as to close the outlet 34.

During a predetermined time, the developer is permitted to flow into hopper 33 until it begins to overflow. The first shutter plate 43 and the second shutter plate 44 are returned to their respective original positions, and at the same time, the developer begins to flow from the outlet 34 through the cylinder 35 at a predetermined flow rate. When developer is not flowing through the cylinder 35, the output of the coil 36 is lowest, but when the developer begins to flow through the cylinder 35, the output increases abruptly. The design of the hopper 33 is such that it holds 50 g of the developer. The procedure permits the preparation of a predetermined toner concentration vs. flow rate curve as discussed in FIGS. 2 and 5. In a predetermined time, all of the developer is discharged from the hopper 33 and the output of the coil 36 decreases abruptly.

The period of time from the initial abrupt change of the oscillating frequency generated by the coil 36 to the final change of the frequency is detected by the frequency detector 37. In other words, the flow rate is detected by the frequency detector 37. A flow rate which has been predetermined experimentally in accordance with the change of active toner concentration is stored as a memory or a program in a reference circuit 38. The output from the frequency detector 37 and that from the reference circuit 38 are compared by a comparison circuit 39, whereby active toner concentration is determined from the flow rate detected by the frequency detector 37 and the rotation of an active toner replenishing roller is controlled so as to replenish active toner until a predetermined active toner concentration is obtained.

The next detection of active toner concentration can be started immediately after this or in a predetermined time. At this time, the first shutter plate 43 and the second shutter plate 44 repeat the above-mentioned movements, respectively.

When non-magnetic resins, glass beads or the like are employed as carrier particles, the above-mentioned magnetic detection method cannot be used. Instead of the method, in FIG. 6, a photoelectric detection apparatus composed of a light emission diode 40 and a light receiving element 43 as shown in phantom in FIG. 6 can be disposed under the outlet 34 of the hopper 33 so that the flow rate of the developer can be detected.

When the flow rate of the developer is measured in advance by comparison with the change of the active toner concentration of the developer, 50 g, or other selected quantities of the developer are placed in the hopper. However, when the amount is too high, it requires too much time to measure the flow rate. When the amount is too low, inaccurate measurements may result. Thus, in accordance with the size of the hopper and the kind of the developer to be measured, the amount of the developer to be placed in the hopper is selected.

Instead of placing a predetermined amount of the developer in the hopper, as illustrated in the apparatus in FIG. 6, the developer may be permitted to flow continuously without closing the first shutter plate 43 and the second shutter plate 44. In the procedure, by measuring flow rate of the developer in a unit time, the toner concentration can be determined easily.

It is important that the diameter of the cylinder 35 is set to be larger than that of the outlet 34 of the hopper 33 so that the amount of the developer which flows out of the outlet 34 is not restricted by the cylinder 35. This is because in the present apparatus, the bulk density of the developer is not measured, but by measuring the amount of the carrier particles in a unit time, the active toner concentration is measured since the amount of the carrier particles which flows out of the outlet 34 varies depending upon the viscosity of the developer and the viscosity varies depending upon the active toner concentration of the developer. In this case, as the developer flow rate detecting means, a Hall element or the like can be employed instead of the non-magnetic cylinder disposed under the hopper 33.

The amount of the developer discharged in a unit time is determined as follows: the period of time from the start of calculation to the end thereof is set by an electric circuit (not shown); the amount of developer which flows in that unit time is determined by the Hall element; the circuit calculates from the Hall element the flow during a unit time, e.g., cm$^3$/sec.

What is claimed is:

1. A method of detecting the active toner concentration of a two-component developer comprising a mixture of carrier particles and toner particles including active and fatigued toner for use in an electrostatic copying apparatus comprising the steps of:
   changing the concentration of active toner in said developer according to a predetermined pattern and measuring the flow rate of said developer for each concentration of active toner to obtain the relationship between the flow rate and the active toner concentration of said developer;
   measuring the flow rate of said developer when its active toner concentration is unknown; and
   determining the unknown active toner concentration of said developer from the measured flow rate and from the predetermined relationship between the flow rate and the active toner concentration of said developer.

2. A method of detecting the active toner concentration of a two-component developer as claimed in claim 1, wherein said flow rate is determined by measuring the period of time during which a predetermined amount of said developer flows past a particular location.

3. A method of detecting the active toner concentration of a two-component developer as claimed in claim 1, wherein said flow rate is determined by measuring the amount of said developer flowing past a particular location in a unit time.

4. A method of detecting the active toner concentration of a two-component developer as claimed in claim 2, wherein said developer is charged into a container having an inlet shutter means initially open and an outlet shutter means initially closed, and when a predetermined amount of said developer has been charged into said container, said inlet shutter means is closed so that no more of said developer is charged into said container, and said outlet shutter is opened to discharge said developer.

5. A method of detecting the active toner concentration of a two-component developer as claimed in claim 2, wherein said developer flow rate is determined by positioning an elastic plate with a strain gauge at said location whereby said plate is bent by a force applied thereto by the flow of said developer past said location to produce an electric current for measurement of said flow rate.

6. A method of detecting the active toner concentration of a two-component developer as claimed in claim 2, wherein said developer flow rate is determined by positioning a non-magnetic cylinder at said location so as to receive a flow of developer therethrough and around which is wound a coil for detecting changes of the magnetic permeability inside said non-magnetic cylinder.

7. A method of detecting the active toner concentration of a two-component developer as claimed in claim 2 or 4, wherein said developer flow rate is determined by positioning a photoelectric detection apparatus composed of at least a light emission element and a light receiving element at opposite sides of said location whereby the beginning and end of the developer flow can be determined by the changes in amount of light reaching said light receiving element.

8. A method of detecting the active toner concentration of a two-component developer as claimed in claim 4, wherein said developer includes magnetic carrier particles and said inlet shutter means and said outlet shutter means each comprises respective electromagnetic elements arranged about respective narrowed tubes connected to said container, and each of said shutter means is closed when the respective electromagnetic element is energized, and is opened when the respective electromagnetic element is deenergized thereby permitting said developer to flow in and out of said container.

9. A method of detecting the active toner concentration of a two-component developer as claimed in claim 4, wherein each of said inlet shutter means and said outlet shutter means comprise one movable shutter plate, respectively.

10. A method of detecting the active toner concentration of a two-component developer as claimed in either claim 4 or claim 9, wherein said developer flow rate is determined by positioning a non-magnetic cylinder at said location so as to receive flow of developer therethrough and around which is wound a coil for detecting changes of the magnetic permeability inside said non-magnetic cylinder.

11. A method of detecting the active toner concentration of a two-component developer as claimed in claim 6, wherein the diameter of said non-magnetic cylinder is larger than that of said outlet of said container.

12. An active toner concentration detector for use with a two-component developer comprising a mixture of carrier particles and toner particles including active and fatigued toner particles for use in an electrostatic copying apparatus comprising:
   a container for holding said developer and having an outlet for said developer in its lower portion;
   means for detecting the rate of flow of developer from said container, said means including a non-magnetic cylinder arranged below said outlet of said container and having an inner diameter greater than the diameter of said outlet, through which said developer flows, and around which is wound a component of an oscillator circuit for producing electric currents having frequencies corresponding to the permeability inside said non-magnetic cylinder;
   a frequency detector for detecting the frequency produced by said oscillator circuit;
   means including a reference circuit for producing a predetermined frequency corresponding to that produced by the flow rate of a desired concentration of active toner of said developer; and
   a comparison circuit for comparing an output from said frequency detector and that from said reference circuit, said comparison circuit being connected to a driving circuit for controlling the replenishment of active toner to be supplied to said developer.

* * * * *